United States Patent [19]
Fuisz

[11] Patent Number: 5,736,154
[45] Date of Patent: Apr. 7, 1998

[54] TRANSDERMAL DELIVERY SYSTEM

[75] Inventor: Richard C. Fuisz, Great Falls, Va.

[73] Assignee: Fuisz Technologies Ltd., Chantilly, Va.

[21] Appl. No.: 613,710

[22] Filed: Mar. 11, 1996

[51] Int. Cl.$^6$ .................................................. A61F 13/00
[52] U.S. Cl. .................................................. 424/449; 424/448
[58] Field of Search .................................. 424/449, 448

[56]   References Cited

U.S. PATENT DOCUMENTS

| | | | |
|---|---|---|---|
| 4,917,676 | 4/1990 | Heiber | 424/449 |
| 5,250,023 | 10/1993 | Lee | 604/20 |
| 5,260,066 | 11/1993 | Wood | 424/447 |
| 5,385,736 | 1/1995 | Kappes et al. | 424/448 |
| 5,403,595 | 4/1995 | Kitchell et al. | 424/501 |
| 5,444,075 | 8/1995 | Minaskanian et al. | 514/327 |
| 5,445,611 | 8/1995 | Eppstein et al. | 604/49 |

*Primary Examiner*—D. Gabrielle Phelan
*Attorney, Agent, or Firm*—Sandra M. Nolan

[57]   ABSTRACT

A drug delivery system useful in treating individuals having maladies requiring topical, subcutaneous and intra-lesional administration of one or more drugs for a prolonged period of time. A method for treating individuals with noduloul-cerative carcinomas using the present invention drug delivery system and intra-lesional administration of interferon to the individual in a controlled, sustained release manner such that long-term therapeutic levels of interferon are provided to the individual. A method of treating an individual having certain skin infections using the present invention drug delivery system including topical and/or subcutaneous administration of one or more drugs to the individual in a controlled, sustained release manner such that long-term therapeutic levels of the drug(s) are provided to the individual.

13 Claims, 1 Drawing Sheet

TRANSDERMAL DELIVERY SYSTEM

TECHNICAL FIELD

The present invention relates to drug delivery systems, and more specifically, to a transdermal drug delivery system, and method of use of same, designed to deliver therapeutically effective dosages of drugs to skin cancers, lesions and infections.

BACKGROUND OF THE INVENTION

For several years, transdermal drug delivery systems have been employed to effectively introduce certain drugs into the bloodstream through unbroken skin. Aside from comfort and convenience, transdermal systems avoid the gastrointestinal tract, the delivery rate control problems and potential toxicity concerns associated with traditional administration techniques, such as oral, intramuscular or intravenous delivery. For example, such systems have proven particularly effective in the delivery of melatonin and other natural hormones to the body, since transdermal delivery mimics the body's own system of secretion. Transdermal delivery has traditionally involved the transport of a drug or drugs across the stratum corneum, the layer of the skin responsible for preventing water loss and the transport of substances through the skin, and into the bloodstream. Transdermal devices known in the art include reservoir type devices including membranes, pressure-sensitive adhesive matrices and skin patches.

Additionally, it has been found that use of transdermal delivery devices in conjunction with ultrasound or iontophoresis aids the delivery of certain drugs. For example, iontophoresis utilizes an electric potential to assist transport of ionic drugs, such as interferon, a protein molecule, from the delivery system through the layers of the skin and into the bloodstream.

It is also known that certain maladies are preferably treated with sustained delivery of one or more drugs to a specific location, such as intra-lesional administration for certain skin carcinomas and topical application for certain skin infections. For example, recently it has been discovered that human natural leukocytic interferon (HNLI), recombinant interferon alpha or beta 2b and/or 2c have been effective in the treatment of noduloulcerative and superficial basal cells carcinomas (BCC). While traditional treatment requires surgical removal of the cancerous area, intralesional treatment of the cancerous site with HNLI has been shown comparably effective without the associated risks of surgery and recurrence.

The typical dosage for such treatment is approximately 1.5×106 IU, 3 times per week for a period of three weeks, requiring at least nine visits to a physician for treatment. One disadvantage to the treatment, however, is the necessary involvement of a physician or other medical personnel with each dosage. Such involvement, while expensive and burdensome, is required since the interferon is delivered in relatively large doses upon each visit, increasing the chances for toxicity and/or other negative reactions to the drug.

While the use of a traditional transdermal delivery system would prevent the need for intensive physician or other medical personnel involvement, and thus the expense and burden of such visits, traditional transdermal delivery systems, which transfer drugs across the stratum corneum layer of the skin and into the bloodstream, are not appropriate for such treatments since the treatment with interferon is intralesional and not systemic in nature.

Another example, tenacious dermatological infections, such as tineas and dermatophytosis, often requires prolonged topical and/or subcutaneous application of one or more drugs for effective treatment of the infection. However, treatment of such infections is typically hampered, if not compromised, because the patient is either unwilling or unable to adhere to the rigorous and lengthy administration schedule of topical and/or subcutaneous drug delivery. Here again, while a traditional transdermal delivery system would make treatment of such infections easier (placement of a patch once a week versus daily or more frequent administration) and more effective (a more constant drug concentration is delivered to the affected area), it is not desired to have the drug(s) passed through to the bloodstream.

Thus a need remains for a drug delivery system, and method of use of same, having the comfort, convenience and delivery control advantages of a traditional transdermal system, but also offering effective transdermal delivery of a drug topically and to the various layers of the skin without the introduction of such drug into the bloodstream.

SUMMARY OF THE INVENTION

The transdermal drug delivery system of the present invention overcomes the foregoing and other problems associated with the prior art by providing quick, easy and accurate local delivery of one or more drugs using a transdermal patch-like device, thus providing the comfort, convenience and control rate of a traditional transdermal system, while effectively applying the drug to the appropriate area of treatment and avoiding introduction of the drug into the bloodstream. As used herein, "transdermal delivery system" shall mean a delivery system capable of transporting one or more drugs across the several layers of the skin, but not passing such drugs through to the bloodstream.

Using the transdermal drug delivery system of the present invention, a transdermal patch is manufactured having several layers. The upper-most layer of the patch comprises an impenetrable polymer or foil, preventing loss of the drugs through the top of the patch. One or more "pouches" containing the drug(s) to be delivered by the patch are sandwiched between the middle layers of the patch. The bottom layer (the layer removably attached to the skin of a patient) of the patch includes one or more regions of an adhesive material. The adhesive material is uncovered or otherwise activated to removably attach the patch to the appropriate location of the skin. Delivery of the drugs takes place for a predetermined period of time before the patch is removed and/or replaced.

Passive transfer of drugs through the patch will occur over time. The amount and concentration of the drug(s) in the pouch(es) determines the rate at which the drug(s) will be delivered to the patient. However, if the drug has a high molecular weight, such as interferon, optimal delivery of the drug can be accomplished with assisted transfer through the use of ultrasound or iontophoresis. Assistance is carefully controlled to facilitate delivery without passage through to the bloodstream.

Utilizing iontophoresis, once the patch is placed in the appropriate location, electrodes are applied to the skin to assist in the transfer of the drug through the layers of the skin. When a voltage is applied to the skin through the electrodes, the delivery of the interferon transdermally is accomplished. The voltage supplied is carefully determined and regulated so that the drug is delivered topically, subcutaneously and/or intra-lesionally, but is not passed through to the bloodstream. The drug is preferably emulsified to facilitate transfer thereof.

Using the novel positioning system and method of co-pending U.S. application, Ser. No. 08/616,173 the patch is easily and properly placed by the patient or other non-health care worker during treatment. The ease of use associated with the delivery system of the present invention, along with the reduced chance for toxicity or other negative reaction to the relatively low, continuous dosage of the drug, allows patients or other non-health care personnel to provide effective treatment without the need for the numerous physician visits associated with traditional forms of treatment.

The present invention also pertains to the use of encapsulating agents to discourage systemic absorption of drugs and to provide optimal tissue levels of said drugs.

The present invention also pertains to a method for treating an individual having certain skin cancers. The method includes intra-lesional administration of interferon to the individual in a controlled, sustained release manner such that long-term therapeutic levels of interferon are provided to the individual. This method is preferably carried out using the drug delivery system described above. Using such a system, the interferon is administered to the individual in an effective and convenient manner.

The present invention also pertains to a method of treating an individual having certain skin infections. The method includes topical and/or subcutaneous administration of one or more drugs to the individual in a controlled, sustained release manner such that long-term therapeutic levels of the drug(s) are provided to the individual. This method is preferably carried out using the drug delivery system described above. Using such a system, the drugs are administered to the individual in an effective and convenient manner.

BRIEF DESCRIPTION OF THE DRAWINGS

For a more complete understanding of the present invention and the advantages thereof, reference is now made to the following description taken in conjunction with the accompanying drawings in which.

DETAILED DESCRIPTION OF THE DRAWINGS

Figure 1:
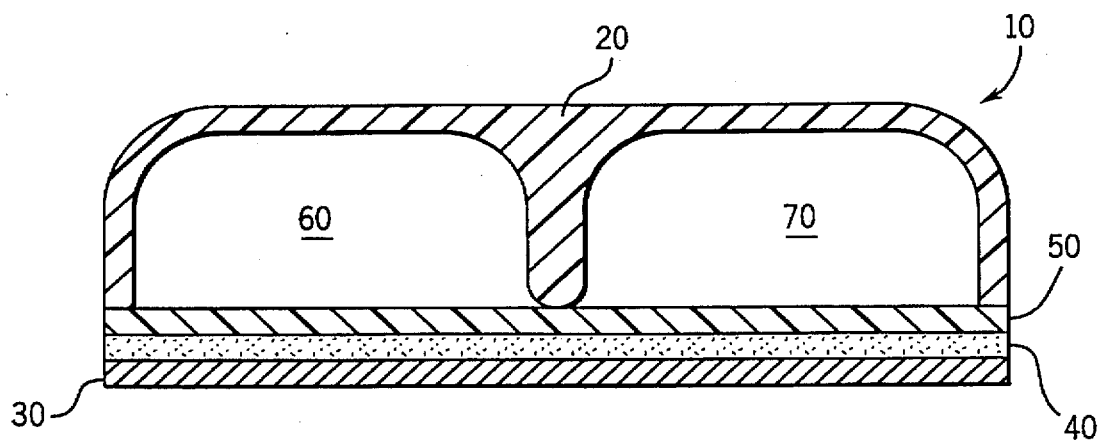
FIG. 1 is a side view of one embodiment of the multi-layered transdermal drug delivery system of the present invention.

Referring to FIG. 1, there is shown a transdermal delivery system 10 of the present invention. The delivery system 10 is a multi-layered polymeric patch, including a top layer 20 and a bottom layer 30. The top layer 20 is preferably made of an impenetrable polymer or foil, to prevent leakage of the drug(s) through the top portion of the delivery system 10. The bottom layer 30 acts as a release sheet which covers one or more areas of an adhesive material 40. When the delivery system 10 is attached to skin, bottom layer 30 will lie immediately adjacent to the skin. The bottom layer 30 is composed of a silanized polyester or other suitable release material and is between 50–100 microns in thickness. The other layers are composed of one or more acrylate polymeric materials.

Figure 2:
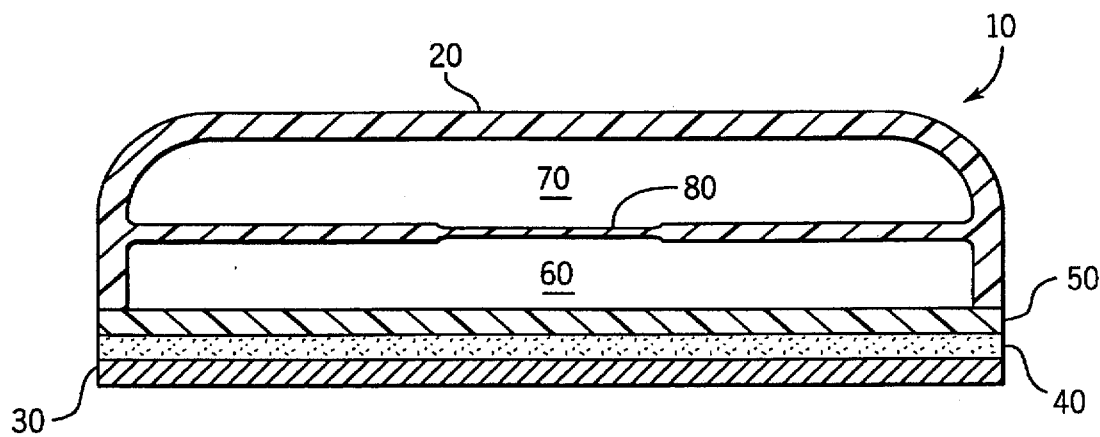
FIG. 2 is a side view of another embodiment of the multi-layered transdermal drug delivery system of the present invention.

The top layer 20 is sealed to a control membrane 50 in such a way so as to create a first chamber 60 and a second chamber 70. The top layer 20 is also sealed to the control membrane 50 in such a way so as to provide a more durable seal between the top layer 20 and the control membrane 50 than the seal between the first chamber 60 and the second chamber 70, the reason for which will be described below. The control membrane 50 provides a barrier to movement of contents of the first chamber 60 and the second chamber 70 alone, and may be made of ethylene vinyl acetate or similar material. In the first chamber 60, the drug to be released by the delivery system 10 is placed. Placed in the second chamber 70 are one or more drug delivery enhancers, such as an aqueous and/or alcoholic solution. Additionally, an encapsulation agent can be placed in the second chamber 70 to prevent systemic absorption of the drug and to provide optimal tissue levels of the drug. Although the first and second chambers described above are located adjacent to each other, it should be noted that they might also lie one on top of the other, as shown in FIG. 2, or take any other suitable relative placement. Alternatively, only one internal chamber may be used, if desired. Additionally, instead of the top layer 20 forming one or more internal chambers, the drug(s) to be delivered can be sealed in a permeable polycarbonate film such that pressure will rupture the film and begin delivery of the drug(s).

In FIG. 2, where like elements are denoted by like reference numerals, another embodiment of the delivery system 10 of the present invention is shown. In this embodiment, a portion of the seal 80 between the first chamber 60 and the second chamber 70 is made weaker than the seal between the top layer 20 and the bottom membrane 50, such that pressure applied to the delivery system 10 will cause the seal to break and the contents of the two chambers to mix.

In use, the release sheet of the bottom layer 30 is removed and the adhesive material 40 releasably attached to the skin of an individual. The exact location for placement of the delivery system 10 preferably is determined using the unique and novel positioning system and method disclosed in co-pending U.S. application, Ser. No. 08/616,173. Using such a positioning system and method, the delivery system 10 includes one or more indelible marks to be aligned with corresponding marks on the area of treatment.

Once properly placed, pressure applied to the delivery system 10 by the individual will cause the weaker seal between the first chamber 60 and the second chamber 70 to break, allowing the contents of the two chambers to mix. Although the control membrane 50 acts as a barrier to either of the contents of the first chamber 60 or second chamber 70 alone, the resultant mixture will penetrate the control membrane 50 and initiate delivery of the drug mixture to the individual.

In one preferred embodiment of the delivery system 10, the first chamber 60 is filled with human natural leukocytic interferon, recombinant interferon alpha or beta 2b and/or 2c, or a combination thereof, for the treatment of noduloulcerative and superficial basal cell carcinomas. The optimum dosage ranged utilized with this embodiment is determined empirically such that appropriate doses are delivered for the desired period of time. In this embodiment, interferon is first homogenized with soybean lecithin (phosphatidylcholine) in the presence of water and an apolar solvent. This microemulsion gel is formed a dynamic network of long and flexible multi-molecular aggregates. Characterized by high viscosity and optical transparency, the lecithin microemulsion gels are ideal for use with the delivery system of the present invention since: (1) they solubilize interferon; (2) they act as a skin penetration enhancer; and (3) they are composed of harmless components such as natural soybean lecithin, fatty acid ester (IPP) and water. One of any number of organic solvents, preferably isopropyl myristate and isopropyl palmitate (IPP), can be used to prepare the lecithin micro-emulsion gels.

In another embodiment of the delivery system 10, the first chamber 60 is filled with griseofulvin, ketoconazole, intraconazole, or the like for the treatment of dermatophytosis or similar skin infections. Again, the optimum dosage range for this embodiment will be determined according to the type of infection, the type of drug(s), or combination thereof, and the treatment period.

Referring now to FIG. 3, there is illustrated the step of an embodiment of the method of the present invention. In step 90, interferon is administered via the drug delivery system described above to an individual having noduloulcerative or superficial basal cell carcinomas or like epithelia tumor for a fixed period of time.

In FIG. 4, there is shown the step of another embodiment of the method of the present invention. In step 100, one or more drugs, such as griseofulvin, ketoconazole, intraconazole, or combinations thereof, are administered via the drug delivery system described above to an individual having a dermatophytosis or similar tenacious skin infection for a fixed period of time.

Although preferred embodiments of the invention have been illustrated in the accompanying drawings and described in the foregoing Detailed Description, it will be understood that the invention is not limited to the embodiments disclosed, but is capable of numerous rearrangements and modifications of parts and elements without departing from the spirit of the invention.

I claim:

1. A dermal multi-layered intralesional drug delivery system consisting essentially of:
   a top layer;
   a control membrane attached to the top layer, forming at least one internal chamber; and
   a bottom layer releasably attached to the control membrane;
   said at least one chamber containing interferon for intralesion, passive treatment of an individual with a carcinoma treatable with intralesional interferon, wherein the interferon does not pass into the bloodstream during delivery.

2. The drug delivery system of claim 1, wherein the control membrane is attached to the top layer such that two or more internal chambers are formed.

3. The drug delivery system of claim 2, wherein attachment between the control membrane and the top layer is stronger than attachment between the internal chambers, such that pressure applied to the delivery system will rupture the attachment between the internal chambers before the attachment between the control membrane and the top layer ruptures.

4. The drug delivery system of claim 1, wherein the interferon is homogenized.

5. The drug delivery system of claim 4, wherein the interferon is homogenized using soybean lecithin.

6. The drug delivery system of claim 5, wherein the interferon is homogenized using soybean lecithin in the presence of water and an apolar solvent.

7. The drug delivery system of claim 1, wherein the interferon is human natural leukocytic interferon.

8. The drug delivery system of claim 1, wherein the interferon is recombinant interferon alpha, beta 2*b* and/or 2*c*.

9. The drug delivery system of claim 1, wherein at least one encapsulating agent is used to prevent systemic absorption of the interferon.

10. A method for treating an individual having a nonduloucerative or basal cell carcinoma, comprising:
    administering interferon intra-lesionally by attachment of at least one passive trandermal patch drug delivery system to an individual, said drug delivery system passively releasing an effective dosage of interferon without drug passage into the bloodstream for a predetermined period of time.

11. The method of claim 10, wherein the interferon is human natural leukocytic interferon.

12. The method of claim 10, wherein the interferon is recombinant interferon alpha, beta 2*b* and/or 2*c*.

13. The method of claim 10, wherein the drug delivery system is the transdermal delivery system of claim 1.

* * * * *